(12) United States Patent
Gottlieb

(10) Patent No.: US 7,419,776 B1
(45) Date of Patent: Sep. 2, 2008

(54) METHOD OF REDUCING PATHOGEN LOAD

(76) Inventor: A. Arthur Gottlieb, deceased, late of Chestnut Hill MA (US); by Marise S. Gottlieb, legal representative, 215 Chestnut Hill Rd., Newton, Middlesex County, MA (US) 02167

( * ) Notice: Subject to any disclaimer, the term of this patent is extended or adjusted under 35 U.S.C. 154(b) by 884 days.

(21) Appl. No.: 09/563,810

(22) Filed: May 1, 2000

Related U.S. Application Data

(60) Provisional application No. 60/132,150, filed on May 3, 1999.

(51) Int. Cl.
- *C12Q 1/00* (2006.01)
- *C12Q 1/70* (2006.01)
- *A61K 38/00* (2006.01)

(52) U.S. Cl. ............... 435/4; 530/300; 435/5; 435/7.2

(58) Field of Classification Search .......... 424/9.1, 424/9.2, 184.1, 185.1, 198.1, 208.1; 514/2, 514/18
See application file for complete search history.

(56) References Cited

U.S. PATENT DOCUMENTS

| | | | | |
|---|---|---|---|---|
| 4,751,216 A * | 6/1988 | Gottlieb | ........................ | 514/18 |
| 5,081,108 A * | 1/1992 | Gottlieb | ........................ | 514/19 |
| 5,093,321 A * | 3/1992 | Gottlieb | ........................ | 514/18 |
| 5,100,663 A * | 3/1992 | Gottlieb | ........................ | 424/88 |
| 6,406,911 B1 * | 6/2002 | Dong | ........................ | 435/455 |

OTHER PUBLICATIONS

Murta et al. 2000. Lymphocyte subpopulations in patients with advanced breast cancer submitted to neoadjuvant chemotherapy. Tumori. vol. 86. No. 5, pp. 403-407. Abstract only.*

Cruse et al. 1995. Illustrated dictionary of immunology. CRC Press, Inc. p. 278.*

Bakker et al. 1995. Treatment of poor prognosis epidemic Kaposi's sarcoma with doxorubicin, bleomycin, vindesine and rh GMCSF. European Journal of Cancer. vol. 31A. No. 2, pp. 188-192.*

Fragola et al. 1998. Correlations between CD4 and RNA response in antiretroviral-naïve patients with very advanced disease (trial ISS 047). Int Conf AIDS. vol. 12, p. 86. Abstract No. 12363.*

Dorland's Illustrated Medical Dictionary, 28th edition. Philadelphia: WB Saunders; 1994, p. 785.*

Gottlieb et al. 10th International Congress on Immunology. Nov. 1-6, 1998. New Dehli, India.*

Gottlieb et al. Annals of Internal Medicine. 1991; 115: 84-91.*

"Hydrolysis", is defined by Dorland's Illustrated Medical Dictionary, 28th edition. Philadelphia: WB Saunders; 1994, p. 785.*

Gottlieb et al. (10th International Congress of Immunology. 1998: 883-99.*

Katz et al. Clinical Infectious Diseases. 2004; 39: 342-348.*

Sizemore et al. Clinical Immunology and Immunopathology. 1995; 76 (3): 308-313.*

* cited by examiner

*Primary Examiner*—Stacy B Chen
(74) *Attorney, Agent, or Firm*—Robert E. Bushnell, Esq.

(57) ABSTRACT

An improved therapy is described for patients suffering from pathological conditions characterized by viral, fungal, bacterial, or protozoal load by which such load is reduced. The invention also alleviates symptoms associated with such pathogen-load-characterized conditions by decreasing the pathogen load.

The present invention accomplishes those objects by administering substances to patients suffering from pathogen load that enhance the function of the patients' immune systems. The substances are known as "immunoamplifiers," a term that refers to the substances' ability to increase cell-mediated immune system response non-specifically.

27 Claims, No Drawings

METHOD OF REDUCING PATHOGEN LOAD

This application claims the benefit of U.S. Provisional Application No. 60/132,150, filed May 3, 1999.

FIELD OF THE INVENTION

This invention concerns a method of reducing pathogen load in a patient, particularly viral load. More particularly, the invention concerns a method of reducing viral load by administering an immunomodulator or "immunoamplifier" to the patient. The invention has particular application in the alleviation of symptoms suffered by HIV (Human Immunodeficiency Virus) and ARC (AIDS-Related Complex) patients, i.e., patients with HIV Disease. The invention also has application to reduction of fungal, bacterial, and protozoal load, and alleviation of symptoms associated with such load.

BACKGROUND OF THE INVENTION

The invention concerns immunodeficient conditions which are caused by or which involve dysfunction of the cell-mediated immune system and which may be reflected by infection with and disease caused by other pathogenic microorganisms which may be viral, bacterial, fungal or protozoal in nature. For example, candidiasis and histoplasmosis are caused by fungal organisms, tuberculosis is caused by a bacterium, and shingles is caused by the re-emergence of Herpes zoster in adults who have previously had chicken pox, the primary manifestation of infection with this virus in childhood.

A typical manifestation of cell-mediated immunity is the delayed type hypersensitivity ("DH") skin reaction. A DH skin reaction is observed when an appropriate antigen is injected intradermally. Within 24 to 48 hours, local inflammation (erythema) and a swelling and thickening (induration) are observed in a sensitive individual. The degree of sensitivity may be measured by the size and severity of the reaction. The DH reaction also presents characteristic histological findings—specifically, perivascular infiltration of leukocytes and monocytes in the inflamed area. The cells seen at the site of a DH reaction are derived from the peripheral blood leukocyte population.

The mechanisms of cell-mediated immunity are as yet incompletely understood. It is known that the cells which mediate the response are capable of responding in a variety of ways to a challenge from an antigen. These responses include: proliferation of cells bearing specific sensitivity to a given antigen; the induction and multiplication of cells mediating a variety of immune functions, including antibody production; and reactions against foreign cells and tumors.

Gottlieb U.S. Pat. No. 4,468,379 disclosed that endogenous materials isolated from human leukocyte dialysates exist that amplify the speed and magnitude of cell-mediated immune system response. These immunoamplifier materials are distinguished from so-called transfer factors in that immunoamplifiers do not transfer to a subject an immune response to a mitogen or antigen to which the subject has not previously been exposed and is not concurrently exposed, while transfer factors are said to do so. Moreover, immunoamplifiers nonspecifically increase cell-mediated immune system responses to mitogens and antigens to which the subject has previously been or concurrently is exposed, while transfer factors are specific to particular antigens.

The material designated "amplifier 1" in the '379 patent was subsequently determined to be a mixture of various things. They include (1) what is referred to subsequently in Gottlieb U.S. Pat. No. 5,081,108 and Gottlieb U.S. Pat. No. 5,100,663 as YG Product, (2) what is referred to in Gottlieb U.S. Pat. No. 5,081,108 as YGG Product, (3) another as-yet undefined or incompletely defined amplifier, (4) various amino acid products, and (5) other materials. The foregoing materials occurred in amplifier 1 in varying relative proportions, depending on the identity of the blood sample from which the sample of amplifier 1 was derived. Such variation appears to reflect the fact that the content of a human blood sample varies from donor to donor and even for the same donor from time to time, depending on the state of the immune system of the donor. The fact that the content of amplifier 1 varied from sample to sample adversely affected the repeatability of experiments directed toward establishing the immunologic activity of amplifier 1. That in turn adversely affected ability to establish product identity, standard dosages, assays, and the like for amplifier 1. These factors have hindered therapeutic utilization of products based on amplifier 1.

Gottlieb U.S. Pat. No. 4,616,079 suggested that amplifiers may act on T-helper cells (T4 cells) in a way that causes them to produce chemical mediators (cytokines) whose effect is to increase the speed and/or magnitude of cell-mediated immune system response to antigens and other means of activating a cell-mediated immune system response. Indicia of this response include DH reaction to recall antigens, production of IL-2 and gamma interferon, and potentiation of cytotoxic cells.

Gottlieb U.S. Pat. No. 4,699,898 and Gottlieb U.S. Pat. No. 5,100,068 disclosed that Tyr-Gly and Tyr-Gly-Gly peptides are immunologically active components in the partially purified dialysate fractions previously described in earlier Gottlieb patents, such as Gottlieb U.S. Pat. No. 4,616,079. The ability of YG Product and YGG Product to affect immune responses has been confirmed in subsequent literature. See, e.g., B. Zacharie et al., Thioamides: Synthesis, stability, and immunologic activities of thioanalogues of Imreg, Preparation of new thioacylating agents using fluorobenzimidazolone derivatives, 42 J. MED. CHEM. 2046 (1999).

Finally, it may be helpful to refer for background purposes to A. Gottlieb et al., Decrease in serum HIV RNA following treatment with a leukocyte dialysate fraction (LDS) that contains N-terminal peptides of the enkephalins and enhances cell-mediated immunity, in INTERNATIONAL CONGRESS OF IMMUNOLOGY, NEW DELHI, INDIA 883-99 (G. P. Talwar et al. eds. 1998)(pub. Monduzzi Editore SpA, Bologna, Italy).

It is known that various diseases and pathological conditions, such as HIV Disease and AIDS, as well as chemotherapy, radiation, and aging, depress the immune system response. A result is increased susceptibility to opportunistic infections, malignancies, and other pathological conditions that a normal immune system would have confronted. Frequently (and for some conditions, invariably), the result is death.

It is now believed that amount of viral load is related to the severity of HIV Disease and AIDS symptoms. By the same token, therapies have been sought that would decrease viral load. As yet, many such therapies have undesirable side effects and/or their effectiveness diminishes after use for a time. It would be desirable to have a therapy for reduction of viral load that caused fewer or no side effects. It would also be desirable to have a therapy for reduction of viral load that did not diminish in effectiveness after use for a time.

It is known that a desired therapeutically active molecule may be delivered by administering to a patient a different molecule that hydrolyzes, as a result of the action of endogenous enzymes, to fractions that include the desired therapeutically active molecule. Hetacillin is a well known example.

Hetacillin breaks down in the human body to ampicillin. A legal controversy ensued internationally, following the introduction of hetacillin, over whether the manufacture, use, and sale of hetacillin infringed patents on ampicillin.

It is known that desired therapeutically active molecules may be degraded by enzymatic hydrolysis, and that such process may sometimes be retarded or prevented by use of the principle of so-called steric hindrance. This term refers to placement of a radical such as methyl in a location where an enzyme might otherwise cause hydrolysis. This principle has been used, largely on a trial and error basis, to create synthetic penicillinase and other hydrolysis-resistant drugs. It is also known to N-methylate the Tyr residue of Tyr-Gly or Tyr-Gly-Gly to inhibit such enzymatic action. It is also known to esterify or amidify the C-terminal carboxyl group to inhibit enzymatic cleavage.

Tyr-Gly and Tyr-Gly-Gly have been sold as chemical reagents (L-tyrosyl-glycine and L-tyrosylglycylglycine) by Sigma Chemical Co., St. Louis, Mo., among others. Tyr-Gly and Tyr-Gly-Gly are not sold in U.S.P. grade, and it is illegal under applicable laws to sell Tyr-Gly or Tyr-Gly-Gly for use as a pharmaceutical. Commercial grade Tyr-Gly and Tyr-Gly-Gly are not considered free of pyrogens, endotoxin, and other pharmaceutically unacceptable constituents. The presence of such pyrogens, endotoxin, and other pharmaceutically unacceptable constituents makes a product unacceptable for use as a drug, as that term is defined by federal statute, both under generally recognized medical principles and under FDA regulations.

Over the years in the literature and in prior Gottlieb patents, the usage of the terms "amplifier", "immunoamplifier", "amplifier of the immune system", and related terms may not have been uniform. It should be understood that "immunoamplifier" as used in this application means the same as those other terms in prior applications and publications.

SUMMARY OF THE PRESENT INVENTION

It is an object of the invention to provide an improved therapy for patients suffering from pathological conditions characterized by viral, fungal, bacterial, or protozoal load by which therapy such load is reduced. In particular it is an object of the invention to provide an improved therapy for reduction of viral load in patients with HIV Disease and AIDS.

It is a further object of the invention to alleviate symptoms associated with such pathogen-load-characterized conditions by decreasing the pathogen load.

The present invention accomplishes those objects by administering substances that enhance the function of the patients' immune systems to patients suffering from or at risk for pathogen load. The substances are known as ☐immunoamplifiers,☐ a term that refers to the substances' ability to non-specifically increase cell-mediated immune system response.

The manner in which the present invention accomplished the objects stated above, as well as other features and benefits of the invention, can better be understood by a review of the following Detailed Description of the Invention.

DETAILED DESCRIPTION OF THE INVENTION

Human test data was gathered with respect to the effect of administering immunoamplifier material to patients.

EXAMPLE 1

AIDS/ARC Conversion in Placebo-Controlled Multicenter Tests of Beta-1.0 Endogenous Purified Leukocyte Dialysate In order to secure clinical data for FDA licensing of Beta-1.0 (an endogenous purified leukocyte dialysate described in U.S. Pats. Nos. 5,081,108, 5,100,068, and 5,100,663) double-blind, randomized, placebo-controlled trials were conducted on a total of 141 ARC ("AIDS-Related Complex") patients at eight testing centers, over a six-month period.

93 patients diagnosed as having ARC received one standard dose of Beta-1.0 biweekly for 26 weeks. 48 patients diagnosed as having ARC received a placebo dose biweekly for 26 weeks. Attending physicians monitored the patients for clinical changes and events.

A standard dose of Beta-1.0 is defined for purposes of this specification to be that which is derived from approximately 125,000 human leukocytes. Ordinarily, it is administered by subcutaneous or intradermal injection. (A standard dose administered biweekly is considered to be an effective dosage amount. An equivalent dosage amount over a different interval or by a different route of administration is also considered to be an effective dosage amount or an equivalent thereof.)

In particular, focus was directed to diagnosis of the conversion to AIDS ("Acquired Immune Deficiency Syndrome") in these ARC patients. This conversion is marked by a significant change in symptoms and clinical status, such as development of *Pneumocytis carinii* pneumonia, tracheobronchial candidiasis, or Kaposi's Sarcoma. Such a clinical event is termed an "endpoint," since it marks the end of ARC and the beginning of AIDS, which appears to be invariably fatal, and is attended by more severe clinical symptoms.

At the end of 26 weeks, endpoints had appeared (a) in 12 of the 48 placebo patients, representing 25% of that population; and (b) in 4 of the 93 patients given Beta-1.0, representing 4% of that population. The rate of ARC/AIDS conversion in patients treated with Beta-1.0 was thus approximately 20% of the conversion rate in placebo patients. Since ARC/AIDS conversion is clinically highly significant, it is believed that the foregoing trial data support the statement that Beta-1.0 reduces progression of HIV Disease.

The patients treated with Beta-1.0 in these trials were also observed to show improved clinical symptomatology, such as lessened weight loss, lessened fever, less coughing, and less diarrhea. Details of this clinical trial are described in Gottlieb, et al., Annals of Internal Medicine, 115: 84-91 (1991).

EXAMPLE 2

Viral Load Assays

Samples of sera from fourteen patients in the clinical trial described in Example 1, supra, were examined (Amplicor Test, Roche) with regard to the effect of Beta-1.0 on the amount of HIV RNA (virus) present in sera drawn from these patients during the course of the clinical trial and frozen for later study. Seven patients who received Beta-1.0 were matched, as a group, on baseline CD4+ cell numbers (mean=299) to seven patients who received placebo (mean=303).

Data on CD4+ cell numbers had been previously collected during the clinical trial. Sera were tested for HIV RNA levels at baseline and at Week 9 of the clinical trial and at the end of the trial (or at the time a clinical endpoint was reached). All of the patients who received Beta-1.0 had a decline in viral load (HIV RNA) from midpoint to the end of the trial, while three of the patients who received placebo showed a decrease in viral load.

Overall, mean viral load was decreased by 30% in the Beta-1.0 treated group compared with an increase of 239% in the placebo group. In the Beta-1.0 treated patients, CD4+ cells fell an average of 23.4 cells per patient over the course of the trial compared with a decline of 32.4 CD4+ cells per patient receiving placebo.

Example 2 describes the ability of the immune supportive agent Beta-1.0 to enable control of the HIV virus as measured by serum RNA level and potentially to control other viruses and pathogens to which patients with depleted or dysfunctional immune systems are at risk. Further, HIV integrates into the genome (DNA) of human cells where it is undetectable by the Amplicor assay, but from which it may be re-expressed. The control of the virus by Beta-1.0 is believed to involve the ability of the immune system to recognize newly produced viral particles or newly infected cells and to clear these from the infected individual.

In individuals with compromised immune systems due to age, cancer, surgery, severe burns, chemotherapy, radiation, viral or other microbial diseases, or other unknown challenges to the immune system, this therapy may be used as a preventative of occurrence of microbial diseases by reconstituting and supporting the function of the immune system. The deterioration of cell-mediated immunity can be measured by a failure to respond to recall antigens using the Delayed-Type Hypersensitivity skin test. The return of cell-mediated immunity can be measured by using the same test in which responsiveness would be restored.

The following present-tense examples are intended to illustrate and summarize the teachings of the preceding examples that describe actual clinical data with over 100 AIDS and ARC patients.

The following terminology is based on similar terminology in earlier Gottlieb U.S. patents described in the Background section of this specification. The terminology refers to YG and YGG (Tyr-Gly and Tyr-Gly-Gly), to molecular modifications of YG and YGG, and to pharmaceutically acceptable salts of these molecules.

"YG Product" means a member of a group consisting of a set of molecular species wherein each molecule contains a YG amino acid residue sequence, and no other amino acid residues. The molecule may be in the form of a simple YG sequence, or the molecule may be methylated, amidified, esterified, alcoholated, acetylated, thioacetylated, or otherwise substituted or covalently modified. YG Product does not include tripeptides or higher polypeptides. However, two YG Products (e.g., two molecules of YG), may be complexed together in the form (YG)Zn++(YG), or they may be dimerized. Such a complex or dimer is not considered a tetrapeptide, but merely two dipeptides complexed together or dimerized.

"YGG Product" means a member of a group consisting of a set of molecular species wherein each molecule contains a YGG amino acid residue sequence, and no other amino acid residues. The molecule may be in the form of a simple YGG sequence, or the molecule may be methylated, amidified, esterified, alcoholated, acetylated, thioacylated, or otherwise substituted or covalently modified. YGG Product does not include dipeptides, tetrapeptides, or higher polypeptides. However, two YGG Products (e.g., two molecules of YGG), or YG Product and YGG Product, may be complexed together or dimerized. Such a complex or dimer is not considered a pentapeptide or hexapeptide.

"Inhibited YG Product" means YG Product that has been mixed, complexed, bound, linked, or otherwise substituted or covalently modified, or otherwise combined with a means for inhibiting cleavage of the YG bond of the molecule by endogenous enzymes; however, the material must still contain a YG amino acid residue sequence and no other amino acid residue sequence. Puromycin and bacitracin are examples of inhibitors that may be mixed with YG Product. It is also known to N-methylate the Tyr residue to inhibit enzymatic action. It is also known to esterify or amidify the C-terminal carboxyl group to inhibit enzymatic cleavage. The products of such expedients are hereinafter termed inhibited YG Product. Inhibited YG Product does not include expanded YG Product, as defined below; the two terms are mutually exclusive, as defined herein.

"Expanded YG Product" means a molecule of the form Tyr-X-Gly, where X is a D-amino acid, such as D-Ala. The term includes amides, esters, salts, and other covalent modifications, etc., as in the case of YG Product. It is known that the insertion of a D-amino acid into Tyr-Gly tends to inhibit cleavage of the Tyr-Gly bond by endogenous enzymes. The terms YG Product and expanded YG Product are mutually exclusive, since the former is a dipeptide and the latter is a tripeptide; also the former has a Tyr-Gly bond and the latter does not.

"Inhibited YGG" Product means YGG Product that has been mixed, complexed, bound, linked, or otherwise substituted or covalently modified, or otherwise combined with a means for inhibiting cleavage of the Tyr-Gly or Gly-Gly bond of the molecule by endogenous enzymes; however, the material must still contain a Tyr-Gly-Gly amino acid residue sequence and no other amino acid residue sequence. Puromycin and bacitracin are examples of inhibitors that may be mixed with YGG Product. As indicated earlier, it is known to N-methylate the Tyr residue to inhibit enzymatic action. It is also known to esterify or amidify the C-terminal carboxyl group to inhibit enzymatic cleavage. The products of such expedients are hereinafter termed inhibited YGG Product. Inhibited YGG Product does not include expanded YGG Product, as defined below; the two terms are mutually exclusive, as defined herein.

"Endogenous YG Product" means YG Product produced within the body.

"Endogenous YGG" Product means YGG Product produced within the body.

"Extraneous-peptide amino acid residue sequences" means any and all amino acid residue sequences except YG and YGG. As used herein, "sequence" refers to a plurality of residues, and the terms excludes a molecule with only a single amino acid residue, such as glycine.

EXAMPLE 3

Fungal Load

A patient with severe candidiasis (infection with the fungus *Candida albicans*) is treated with drugs from the usual antifungal armamentarium such as Fluconazole for two weeks without effect.

The antifungal treatment is continued, but now, the patient is treated concurrently with YG Product. The candidiasis clears. A dose is administered by one of the following routes: intradermally, subcutaneously, orally, transmucosally, sublingually, or transdermally. The dosage amount is biologically equivalent to that derived from approximately 125,000 human leukocytes administered biweekly, and is increased or decreased as appropriate for less or more frequent administration.

Because resistant candidiasis is known to be associated with immune deficiency, treatment with YG Product is continued and the patient remains free of fungal infection.

The use of immunoenhancing substances in conjunction with standard anti-microbial therapeutics (antibacterial, antifungal, antiviral, or protozoal) assists in ability of these standard agents to control specific diseases caused by the microbial pathogens by enhancing the ability of the human immune system to respond in a more normal manner. Beta-1.0, YG Product and YGG Product are such immunoenhancing agents. It is known that antimicrobial agents, by themselves, do not totally eradicate or control the microbial pathogen but require a functioning immune system to accomplish the task. The use of Beta-1.0, YG Product or YGG Product may decrease the dose of antimicrobial agent required to eradicate the pathogenic organism and may lengthen the time required for antimicrobial therapy. This decreased exposure to standard antimicrobial drugs, each of which is known to have associated toxicity, could decrease side effects experienced by the patient and also decrease the emergence of organisms resistant to the antimicrobial drugs.

Additional examples would include the use of the instant materials in addition to standard antifungal, antibacterial, antiviral, or other antimicrobial therapy, as appropriate, in conditions such as histoplasmosis, tuberculosis, especially in multiple drug resistant tuberculosis, gonorrhea, or infection with Staphylococcus aureus.

The dosage amount is as described in Example 3.

EXAMPLE 4

Viral Load

Shingles

A patient presents with shingles. The patient is known to have had chicken pox (*Herpes zostez*) as a child, but now the virus, which has been present in the patient's body but which has remained under control, has reemerged, causing a painful rash. Shingles often occurs in association with other diseases, with chemotherapy, and during periods of stress, all of which cause a decline in cell-mediated immune function. It is this decline which allows the virus to become uncontrolled and to reemerge.

The patient is treated with YG Product administered every two weeks by intradermal injection. Shingles is cleared within 4 weeks. Treatment is continued for two months and there is no recurrence when treatment is discontinued.

EXAMPLE 5

Viral Load

Shingles/Chemotherapy

A patient receiving chemotherapy for prostate cancer presents with shingles. The patient is known to have had chicken pox (*Herpes zoster*) as a child, but now the virus, which has been present in the patient's body but which has remained under control, has reemerged, causing a painful rash. Shingles often occurs in association with other diseases, with chemotherapy, and during periods of stress, all of which cause a decline in cell-mediated immune function. It is this decline which allows the virus to become uncontrolled and to reemerge.

The patient is treated with YG Product. Shingles is cleared within 4 weeks. Treatment is continued for two months. Once treatment is discontinued, the shingles recurs. Treatment with YG Product is restarted and the shingles clears. Treatment with YG is continued until chemotherapy is complete and the immune system recovers. There is no recurrence.

EXAMPLE 6

Prophylaxis

A patient is diagnosed as having prostate cancer. Surgery and chemotherapy are anticipated. The physician knows that individuals with cancer often have reduced immune function. Further, the stress of surgery and the chemotherapeutic drugs cause immune dysfunction, resulting in increased susceptibility to microbial pathogens. If an infection occurs, it will be more difficult to treat with standard therapies because the immune system is not able to assist in clearing the infection. The physician elects to treat the patient with YG Product prior to surgery to enhance cell-mediated immune function. He continues treatment during the recovery period and period of chemotherapy. The occurrence of infection, including opportunistic infection, is avoided.

EXAMPLE 7

Extended Prophylaxis

An 80 year old woman is admitted to the hospital for surgical repair of a fractured hip. It is well known that she is at high risk of developing a pneumonia secondary to a pneumococcal (or staphylococcal or streptococcal) infection following the trauma, anesthesia, and blood loss during surgery. Her physician knows that such nosocomial infections, even with the use of potent antibiotics, have a high rate of morbidity, increasing the length of hospitalization, and/or death. It is well known that antibiotic agents are limited in their effectiveness and that a properly functioning immune system is required to effectively eliminate pathogenic microbes. Further, the decline in immune function with aging and especially as a result of surgical stress increases the risk of infection.

Her physician elects to treat the patient, upon admission, with synthetic YG Product or synthetic YGG Product to enhance the ability of her immune system to protect against infection and subsequent disease associated with the high likelihood of exposure to pathogenic organisms under these circumstances. Moreover, since there is a rehabilitation and recovery period in an extended care facility, he elects to continue such treatment through recovery.

It is believed that ensuring an adequate immune response to these and other more virulent pathogens decreases the number of infections, reduces the need for antibiotics, reduces the required period of treatment with antibiotics, if needed, and reduces the development of antibiotic resistant pathogens.

EXAMPLE 8

Maintenance of Immune Function

A properly functioning cell-mediated immune system is important to provide resistance to disease originating from exogenous and endogenous infective organisms, pathogenic or otherwise, and from diseases which may be associated with disorders of human immunity. Such diseases include cancers or autoimmune disorders which may be triggered by an infectious organism, or otherwise related to infectious organisms or a disease made more complicated by superimposed infections.

A patient has a family history of Type I (insulin-dependent) diabetes mellitus and is potentially at risk of that disease being triggered by a viral (or other) infection. The patient's physician regularly monitors the competence of the patient's cell-mediated immune system by testing the ability to demonstrate an appropriate DH response to recall antigen. The physician reasons that the onset of Type I diabetes mellitus can be prevented if cell-mediated immune function is maintained.

After a particularly stressful period, the physician notes that the patient's DH response is subnormal, an indicator that the patient is at risk for an infection, and thus for onset of diabetes. The physician treats the patient with YG product at a dosage equivalent to that which would be derived from 125,000 leukocytes administered biweekly.

Treatment continues until the DH response returns to normal. Infection and disease are avoided. Periodic monitoring of DH to recall antigen is continued.

GENERAL CONCLUDING REMARKS

As the preceding examples and discussion show, the invention can be practiced with a genus of products characterized by the presence of Tyr and Gly amino acid residues, with optional admixture with other products and with optional modification of certain parts of the structure.

While the invention has been described in connection with specific and pre-ferred embodiments thereof, it is capable of further modifications without departing from the spirit and scope of the invention. This application is intended to cover all variations, uses, or adaptations of the invention, following, in general, the principles of the invention and including such departures from the present disclosure as come within known or customary practice within the art to which the invention pertains, or as are obvious to persons skilled in the art, at the time the departure is made. It should be appreciated that the scope of this invention is not limited to the detailed description of the invention hereinabove, which is intended merely to be illustrative, but rather comprehends the subject matter defined by the following claims.

As used in the claims, the term "Selected Immunoamplifier" means a product that is one of the following immunoamplifiers or that is a mixture of a plurality of the following immunoamplifiers: purified Leukocyte Dialysate Subfraction; YG that has been methylated, acetylated, thioacylated, amidified, esterified, or alcoholated YG; a covalent modification to or covalent addition to YG such that the modification or addition is adapted to inhibit hydrolysis or increase bioactivity; YGG that has been methylated, acetylated, thioacylated, amidified, esterified, or alcoholated YGG; a covalent modification to or covalent addition to YGG such that the modification or addition is adapted to inhibit hydrolysis or increase bioactivity; or a pharmaceutically acceptable salt of any of the foregoing.

The subject matter claimed is:

1. A method for decreasing pathogen load in a patient having a pathogen load, said method comprising:
   administering Beta-1.0 for decreasing said pathogen load;
   detecting said pathogen load in said patient to check whether said pathogen load is decreased; and
   continuing the administering step and the detecting step at least until the pathogen load is decreased.

2. The method of claim 1, wherein said pathogen is a virus, a fungus, a bacterium, or a protozoon.

3. The method of claim 1, wherein said pathogen is Candida and the patient suffers from candidiasis.

4. The method of claim 1 wherein said pathogen is Herpes zoster and the patient suffers from shingles.

5. The method of claim 1, wherein said pathogen is Herpes simplex and the patient suffers from genital herpes.

6. The method of claim 1, wherein said pathogen is Mycobacterium tuberculosis and the patient suffers from tuberculosis.

7. The method of claim 1, wherein said pathogen is Pneumococus pneumonia and the patient suffers or is at risk from pneumonia.

8. The method of claim 1, wherein said pathogen is Hepatitis B Virus and the patient suffers from hepatitis B.

9. The method of claim 1, wherein said pathogen is HIV and the patient is HIV positive or has HIV Disease or AIDS.

10. A method for decreasing pathogen load in a patient having a pathogen load, said method comprising:
    orally, transmucosally, sublingually, transdermally, subcutaneously, intradermally, or by other comparable method, administering a product to the patient, wherein said product is selected from the group consisting of YG dipeptide, YGG tripeptide, a pharmaceutically acceptable salt of any of the foregoing, and a combination thereof;
    detecting said pathogen load in said patient to check whether said pathogen load is decreased; and
    continuing the administering step and the detecting step at least until the pathogen load is decreased.

11. The method of claim 10, wherein said pathogen is a virus, a fungus, a bacterium, or a protozoon.

12. The method of claim 10, wherein said pathogen is HIV and the patient is HIV positive or has HIV Disease or AIDS.

13. A method of decreasing HIV viral load in an HIV Disease or AIDS patient, said method comprising:
    administering a product to the patient, wherein said product is selected from the group consisting of YG dipeptide, YGG tripeptide, a pharmaceutically acceptable salt of any of the foregoing, and a combination thereof;
    detecting said HIV viral load in said patient to check whether said HIV viral load is decreased; and
    continuing the administering step and the detecting step at least until the HIV viral load is decreased.

14. A method for treating a pathogen infected patient, said method comprising:
    administering a product to the patient, wherein said product is selected from the group consisting of YG dipeptide, YGG tripeptide, a pharmaceutically acceptable salt of any of the foregoing, and a combination thereof;
    detecting the pathogen load in said patient to check whether said pathogen load is increased; and
    continuing the administering step and the detecting step at least until said pathogen load is not increasing.

15. The method of claim 14 wherein said pathogen is a virus, a fungus, a bacterium, or a protozoa.

16. The method of claim 14 wherein said pathogen is Candida and the patient suffers from candidiasis.

17. The method of claim 14 wherein said pathogen is Herpes zoster and the patient suffers from shingles.

18. The method of claim 14 wherein said pathogen is Herpes simplex and the patient suffers from genital herpes.

19. The method of claim 14 wherein said pathogen is Mycobacterium tuberculosis and the patient suffers from tuberculosis.

20. The method of claim 14 wherein said pathogen is Pneumococus pneumonia and the patient suffers from pneumonia.

21. The method of claim 14, wherein said pathogen is Hepatitis B Virus and the patient suffers from hepatitis B.

22. The method of claim 14, wherein said pathogen is HIV and the patient is HIV positive or has HIV Disease or AIDS.

23. A method for treating a patient having a pathogen load, said method comprising:
    administering orally, transmucosally, sublingually, transdermally, subcutaneously, intradermally, or by other comparable method, a product to the patient, wherein said product is selected from the group consisting of YG dipeptide, YG dipeptide which is methylated, acetylated, thioacylated, amidified, esterified, or alcoholated, YG dipeptide which is modified by covalent modification or covalent addition to prevent said YG dipeptide from being hydrolyzed or to increase bioactivity of said YG dipeptide, YGG tripeptide, YGG tripeptide which is methylated, acetylated, thioacylated, amidified, esterified, or alcoholated, YGG tripeptide which is modified by covalent modification or covalent addition to prevent said YGG tripeptide from being hydrolyzed or increase bioactivity of said YGG tripeptide, a pharmaceutically acceptable salt of any of the foregoing, Beta 1.0, and a combination thereof;
    detecting said pathogen load in said patient to check whether said pathogen load is decreased; and
    continuing the administering step and the detecting step at least until the pathogen load is decreased.

24. A method of decreasing HIV viral load in an HIV Disease or AIDS patient, said method comprising:
    orally, transmucosally, sublingually, transdermally, subcutaneously, intradermally, or by other comparable method, administering a product to the patient, wherein said product is selected from the group consisting of YG dipeptide, YG dipeptide which is methylated, acetylated, thioacylated, amidified, esterified, or alcoholated, YG dipeptide which is modified by covalent modification or covalent addition to prevent said YG dipeptide from being hydrolyzed or to increase bioactivity of said YG dipeptide, YGG tripeptide, YGG tripeptide which is methylated, acetylated, thioacylated, amidified, esterified, or alcoholated, YGG tripeptide which is modified by covalent modification or covalent addition to prevent said YGG tripeptide from being hydrolyzed or to increase bioactivity of said YGG tripeptide, a pharmaceutically acceptable salt of any of the foregoing, Beta 1.0, and a combination thereof;
    detecting said HIV viral load in said patient to check whether said HIV viral load is decreased; and
    continuing the administering step and the detecting step at least until the HIV viral load is decreased.

25. A method for treating a pathogen infected patient, said method comprising:
    orally, transmucosally, sublingually, transdermally, subcutaneously, intradermally, or by other comparable method, administering a product to the patient, wherein said product is selected from the group consisting of YG dipeptide, YG dipeptide which is methylated, acetylated, thioacylated, amidified, esterified, or alcoholated, YG dipeptide which is modified by covalent modification or covalent addition to prevent said YG dipeptide from being hydrolyzed or increase bioactivity of said YG dipeptide, YGG tripeptide, YGG tripeptide which is methylated, acetylated, thioacylated, amidified, esterified, or alcoholated, YGG tripeptide which is modified by covalent modification or covalent addition to prevent said YGG tripeptide from being hydrolyzed or increase bioactivity of said YGG tripeptide, a pharmaceutically acceptable salt of any of the foregoing, Beta 1.0, and a combination thereof;
    detecting the pathogen load in said patient to check whether said pathogen load is increased; and
    continuing the administering step and the detecting step at least until said pathogen load is not increasing.

26. A method for treating a pathogen infected patient, said method comprising:
    orally, transmucosally, sublingually, transdermally, subcutaneously, intradermally, or by other comparable method, administering Beta 1.0 to the patient;
    detecting the pathogen load in said patient to check whether said pathogen load is decreased; and
    continuing the administering step and the detecting step at least until said pathogen load is decreased.

27. A method for treating a pathogen infected patient, said method comprising:
    administering Beta 1.0 to the patient;
    detecting the pathogen load in said patient to check whether said pathogen load is increased; and
    continuing the administering step and the detecting step at least until said pathogen load is not increasing.

* * * * *